US 12,114,896 B2

(12) United States Patent
Biedermann (10) Patent No.: US 12,114,896 B2
(45) Date of Patent: Oct. 15, 2024

(54) POLYAXIAL BONE ANCHORING DEVICE AND SYSTEM OF AN INSTRUMENT AND A POLYAXIAL BONE ANCHORING DEVICE

(71) Applicant: BIEDERMANN TECHNOLOGIES GMBH & CO. KG, Donaueschingen (DE)

(72) Inventor: Timo Biedermann, Trossingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 25 days.

(21) Appl. No.: 17/736,663

(22) Filed: May 4, 2022

(65) Prior Publication Data

US 2022/0330989 A1    Oct. 20, 2022

Related U.S. Application Data

(63) Continuation of application No. 16/665,510, filed on Oct. 28, 2019, now Pat. No. 11,344,334, which is a (Continued)

(30) Foreign Application Priority Data

Aug. 24, 2016    (EP) ..................... 16185554

(51) Int. Cl.
*A61B 17/70*    (2006.01)
*A61B 17/00*    (2006.01)

(52) U.S. Cl.
CPC ...... *A61B 17/7032* (2013.01); *A61B 17/7037* (2013.01); *A61B 17/7076* (2013.01); (Continued)

(58) Field of Classification Search
CPC ........ A61B 17/70–7046; A61B 17/7074–7092
See application file for complete search history.

(56) References Cited

U.S. PATENT DOCUMENTS 5,217,497 A    6/1993 Mehdian
5,375,956 A    12/1994 Pennig
(Continued)

FOREIGN PATENT DOCUMENTS

CN    101143108 A    3/2008
CN    101754725 A    6/2010
(Continued)

OTHER PUBLICATIONS

European Search Report for European Application No. 16185554.9 dated Feb. 2, 2017 and mailed Feb. 15, 2017 (8 pages).

*Primary Examiner* — Eduardo C Robert
*Assistant Examiner* — Steven J Cotroneo
(74) *Attorney, Agent, or Firm* — Lewis Roca Rothgerber Christie LLP (57) ABSTRACT

A bone anchoring device includes a receiving part having a first end with an end surface, a second end, a recess at the first end for receiving a rod, and a flexible head receiving portion at the second end for pivotably holding a head of a bone anchoring element, and a clamping ring positionable around the head receiving portion and movable from a first position where the head is pivotable relative to the receiving part, to a second position where the clamping ring exerts a radial force onto the head receiving portion to lock the head. The receiving part further includes a first engagement structure at or adjacent the end surface extending radially outwardly from an outer surface of the receiving part, such that a width of the receiving part including the first engagement structure is at least as wide as a maximum width of the clamping ring.

20 Claims, 9 Drawing Sheets

Related U.S. Application Data continuation of application No. 15/669,541, filed on Aug. 4, 2017, now Pat. No. 10,492,833.

(60) Provisional application No. 62/379,115, filed on Aug. 24, 2016.

(52) U.S. Cl.
CPC ........ *A61B 17/708* (2013.01); *A61B 17/7083* (2013.01); *A61B 2017/00526* (2013.01)

(56) References Cited

U.S. PATENT DOCUMENTS

| | | | |
|---|---|---|---|
| 5,549,608 A * | 8/1996 | Errico | A61B 17/7037 606/264 |
| 5,575,792 A | 11/1996 | Errico | |
| 5,586,984 A | 12/1996 | Errico | |
| 5,672,176 A | 9/1997 | Biedermann et al. | |
| 5,728,098 A | 3/1998 | Sherman et al. | |
| 6,254,602 B1 | 7/2001 | Justis | |
| 6,273,888 B1 | 8/2001 | Justis | |
| 6,299,616 B1 | 10/2001 | Beger | |
| 6,582,436 B2 | 6/2003 | Schlapfer et al. | |
| 6,743,231 B1 | 6/2004 | Gray et al. | |
| 7,947,065 B2 | 5/2011 | Hammill, Sr. | |
| 7,955,359 B2 | 6/2011 | Matthis et al. | |
| 7,967,826 B2 | 6/2011 | Colleran et al. | |
| 7,988,694 B2 | 8/2011 | Barrus et al. | |
| 8,075,603 B2 | 12/2011 | Hammill, Sr | |
| 8,298,275 B2 | 10/2012 | Rezach | |
| 8,506,609 B2 | 8/2013 | Biedermann et al. | |
| 8,506,610 B2 | 8/2013 | Biedermann | |
| 8,568,458 B2 | 10/2013 | Matthis et al. | |
| 8,636,781 B2 * | 1/2014 | Biedermann | A61B 17/7035 606/279 |
| 8,663,298 B2 | 3/2014 | Keyer et al. | |
| 9,005,260 B2 * | 4/2015 | Dauster | A61B 17/7032 606/301 |
| 9,050,148 B2 * | 6/2015 | Jackson | A61B 17/7037 |
| 9,144,441 B2 | 9/2015 | Biedermann et al. | |
| 9,173,684 B2 * | 11/2015 | Biedermann | A61B 17/7032 |
| 9,333,016 B2 * | 5/2016 | Biedermann | A61B 17/7037 |
| 9,681,895 B2 | 6/2017 | Biedermann et al. | |
| 10,492,833 B2 * | 12/2019 | Biedermann | A61B 17/708 |
| 2004/0254576 A1 | 12/2004 | Dunbar, Jr. et al. | |
| 2005/0080415 A1 | 4/2005 | Keyer et al. | |
| 2005/0096653 A1 | 5/2005 | Doubler et al. | |
| 2005/0228385 A1 | 10/2005 | Iott | |
| 2006/0074445 A1 | 4/2006 | Gerber et al. | |
| 2006/0111715 A1 * | 5/2006 | Jackson | A61B 17/7032 606/279 |
| 2006/0173454 A1 * | 8/2006 | Spitler | A61B 5/107 606/279 |
| 2006/0247658 A1 | 11/2006 | Pond | |
| 2007/0161987 A1 | 7/2007 | Capote | |
| 2007/0270842 A1 | 11/2007 | Bankoski | |
| 2008/0015576 A1 | 1/2008 | Whipple | |
| 2008/0108992 A1 * | 5/2008 | Barry | A61B 17/7037 606/103 |
| 2008/0161859 A1 | 7/2008 | Nilsson | |
| 2009/0036934 A1 * | 2/2009 | Biedermann | A61B 17/7037 606/301 |
| 2009/0062860 A1 | 3/2009 | Frasier | |
| 2009/0105715 A1 | 4/2009 | Belliard | |
| 2009/0105756 A1 | 4/2009 | Richelsoph | |
| 2009/0149887 A1 | 6/2009 | Schlaepfer et al. | |
| 2010/0030135 A1 | 2/2010 | Mitchell | |
| 2010/0131017 A1 | 5/2010 | Farris et al. | |
| 2010/0160977 A1 | 6/2010 | Gephart et al. | |
| 2010/0168800 A1 | 7/2010 | Biedermann et al. | |
| 2010/0204735 A1 | 8/2010 | Gephart et al. | |
| 2011/0060374 A1 | 3/2011 | Sicvol et al. | |
| 2011/0125196 A1 | 5/2011 | Quevedo et al. | |
| 2011/0276098 A1 | 11/2011 | Biedermann et al. | |
| 2012/0046699 A1 | 2/2012 | Jones et al. | |
| 2012/0059426 A1 | 3/2012 | Jackson | |
| 2012/0095516 A1 | 4/2012 | Dikeman | |
| 2012/0179209 A1 | 7/2012 | Biedermann et al. | |
| 2012/0203288 A1 | 8/2012 | Lange et al. | |
| 2012/0209332 A1 | 8/2012 | Janowski | |
| 2013/0085536 A1 * | 4/2013 | Biedermann | A61B 17/7076 606/328 |
| 2013/0096623 A1 | 4/2013 | Biedermann et al. | |
| 2013/0110179 A1 | 5/2013 | Barrus et al. | |
| 2013/0123860 A1 | 5/2013 | Biedermann et al. | |
| 2013/0123861 A1 | 5/2013 | Biedermann et al. | |
| 2014/0031880 A1 * | 1/2014 | Biedermann | A61B 17/7035 606/305 |
| 2014/0214097 A1 | 7/2014 | Jackson et al. | |
| 2014/0358182 A1 | 12/2014 | Puekert | |
| 2015/0119940 A1 | 4/2015 | Jackson et al. | |
| 2015/0182265 A1 | 7/2015 | Biedermann et al. | |
| 2016/0030090 A1 | 2/2016 | Webb | |
| 2016/0220281 A1 | 8/2016 | Biedermann et al. | |
| 2017/0020574 A1 | 1/2017 | Biedermann et al. | |

FOREIGN PATENT DOCUMENTS

| | | |
|---|---|---|
| JP | 2007-506525 A | 3/2007 |
| WO | WO 2005/030070 A1 | 4/2005 |
| WO | WO 2011/043799 A1 | 4/2011 |
| WO | WO 2011/077511 A1 | 6/2011 |
| WO | WO 2015/069873 A1 | 5/2015 |

* cited by examiner

POLYAXIAL BONE ANCHORING DEVICE AND SYSTEM OF AN INSTRUMENT AND A POLYAXIAL BONE ANCHORING DEVICE

CROSS-REFERENCE TO RELATED APPLICATION(S)

This application is a continuation of U.S. patent application Ser. No. 16/665,510, filed Oct. 28, 2019, which is a continuation of U.S. patent application Ser. No. 15/669,541, filed Aug. 4, 2017, now U.S. Pat. No. 10,492,833, which claims the benefit of U.S. Provisional Patent Application Ser. No. 62/379,115, filed Aug. 24, 2016, and claims priority from European Patent Application EP 16 185 554.9, filed Aug. 24, 2016, the contents of which are hereby incorporated by reference in their entirety.

BACKGROUND

Field

The present invention relates to a polyaxial bone anchoring device and to a system of an instrument and a polyaxial bone anchoring device. The polyaxial bone anchoring device comprises a receiving part for coupling a rod to a bone anchoring element and a clamping ring. The receiving part has a flexible head receiving portion and the clamping ring is configured to be arranged around the head receiving portion. When the clamping ring is around the head receiving portion, the clamping ring can assume a locking position wherein the clamping ring exerts a force onto the head receiving portion such that an inserted head is locked, and a non-locking position wherein an inserted head is pivotable relative to the receiving part.

Description of Related Art

US 2013/0085536 A1 describes a polyaxial bone anchoring device including a receiving part with a rod receiving portion and a head receiving portion for introducing and clamping of the head of a bone anchoring element and a locking ring configured to be arranged around the head receiving portion. The locking ring includes an engagement structure in the form of circumferentially extending ribs for engagement with a tool to allow the locking ring to be moved out of the locking position, i.e. releasing the locking mechanism. This enables a surgeon or other practitioner to carry out revisions or further positioning or re-positioning of the angular position of a receiving part with respect to the bone anchoring element.

US 2011/0060374 A1 describes a percutaneous access device which includes an inner tube and an outer tube and also describes a bone anchor having a distal bone engaging portion and a receiving member having a recess for receiving a spinal fixation element. The proximal end of the receiving member may have an arcuate groove formed on an exterior surface thereof to facilitate connection of an instrument to the receiving member.

SUMMARY

Embodiments of the invention provide a polyaxial bone anchoring device that allows an improved handling during surgery, and provide a system including an instrument adapted for use with such a polyaxial bone anchoring device.

According to embodiments of the invention, a receiving part of a polyaxial bone anchoring device comprises a first engagement structure configured to be engaged by a corresponding engagement portion of an instrument, wherein the first engagement structure is positioned on an outer surface of the receiving part directly at or adjacent to an end surface of a top end of the receiving part. The end surface may for example be an annular end surface of a leg of the receiving part formed by a rod receiving channel. The positioning of the engagement structure directly at or adjacent the first end allows to easily find a receiving part and an aligned attachment position for an instrument in an incision or hole formed in a tissue of a human body.

Due to such an arrangement of the first engagement structure, the receiving part may be engaged by an instrument at a position more distant away from an implant site in the bone and closer to the operator. Accordingly, a need for sufficient space for the receiving part and instrument within an incision or hole formed in the tissue of the human body may be reduced. In other words, less body tissue may be affected by removal when creating the incision and a visual control of operation steps during surgery may be improved. If the engagement structure is formed as a rib circumferentially extending along the end face, the instrument having a corresponding circumferential notch may be applied to the receiving part with an easy find and rotation process.

The polyaxial anchoring device may further comprise a clamping ring, which, when moved relative to the receiving part in an axial direction, locks or unlocks the head of an anchoring element received in the receiving part. In such an embodiment, there may further be provided a second engagement structure arranged at upwardly projecting arms provided at the clamping ring. Due to such arms, even the second engagement structures may be in a position close to the top end and the first engagement portion of the receiving part. An instrument configured to cooperate with the receiving part to effect locking and unlocking of an anchoring element received in the receiving part may be provided with a corresponding engagement portion.

In a further embodiment, a third engagement structure of the receiving part cooperates with a further engagement portion of the instrument. The further engagement portion includes an abutment mechanism (a stop) and optionally a self-locking mechanism. The abutment mechanism is realized by an abutment face which serves as an endpoint of an engaging movement, while the self-locking mechanism may be realized by an inclined section of a guiding wall portion of the further engagement portion of the instrument which creates an increasing amount of friction during engagement by the third engagement portion.

The abutment mechanism allows to establish a correct alignment between the instrument and the polyaxial bone anchoring device while the self-locking mechanism advantageously allows to maintain and control the locked engaged positon and to avoid unintentional disengagement.

BRIEF DESCRIPTION OF THE DRAWINGS

Further features and advantages of the invention will become apparent from the description of embodiments by means of the accompanying drawings. In the drawings:

FIG. 3a shows a perspective view from the top of a receiving part of FIG. 1;

FIG. 3b shows a perspective view from the bottom of the receiving part of FIG. 1;

FIG. 4a shows a cross-sectional view of the receiving part of FIGS. 3a and 3b along a line A-A in FIG. 4c;

FIG. 4b shows an enlarged view of the head receiving portion of the receiving part of FIG. 4a;

FIG. 4c shows a top view of the receiving part of FIG. 4a;

FIG. 16b shows a horizontal cross sectional view taken along line B-B in FIG. 16a;

FIG. 16c shows a horizontal cross sectional view taken along line C-C in FIG. 16a;

DETAILED DESCRIPTION

Figure 1:
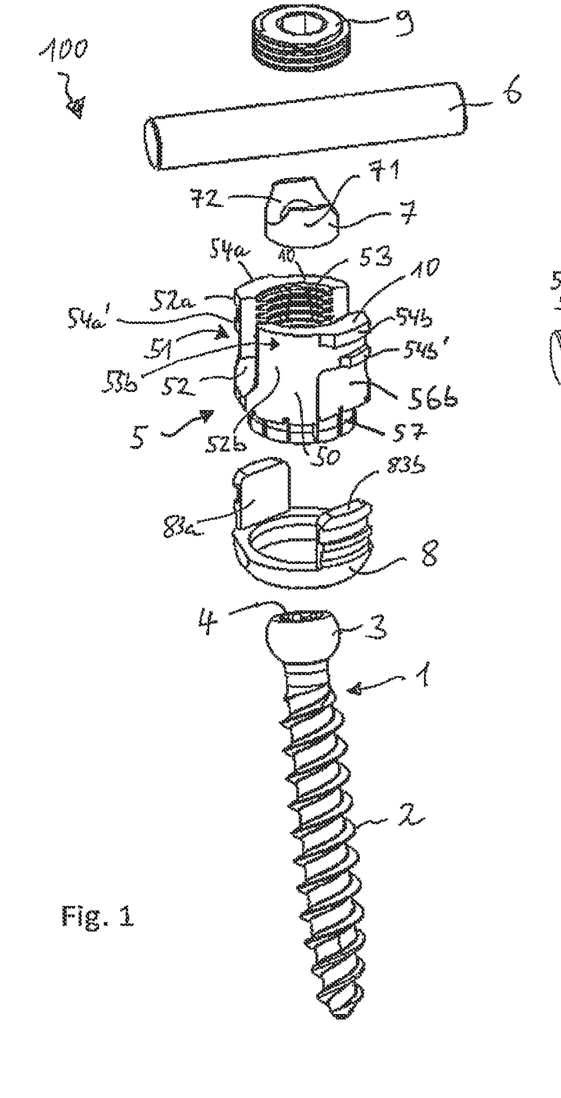
FIG. 1 shows an exploded perspective view of an embodiment of a polyaxial bone anchoring device according to the invention.
Figure 2:
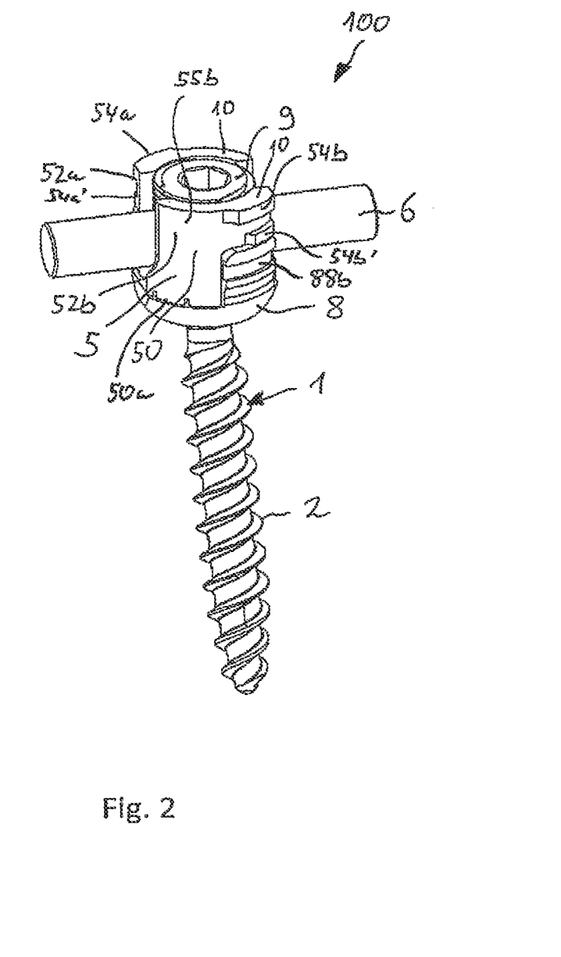
FIG. 2 shows a perspective view of the polyaxial bone anchoring device of FIG. 1 in an assembled state.

As shown in FIGS. 1 and 2, a bone anchoring device according to an embodiment of the invention includes a bone anchoring element 1 in the form of, for example, a bone screw having a shank 2 with a threaded portion and a head 3 with a spherically-shaped outer surface portion. The head 3 may have a recess 4 for engagement with a driver or tool. The bone anchoring device also includes a receiving part 5 for receiving a rod 6 to be connected to the bone anchoring element 1. Further, a pressure member 7 may be provided in the receiving part 5 for exerting pressure onto the head 3 of the bone anchoring element 1. In addition, the bone anchoring device includes a clamping ring 8 that is mountable to the receiving part 5 for compressing a portion of the receiving part 5 to exert pressure onto the pressure member 7 and in turn onto the head 3. Lastly, the bone anchoring element also includes a fixation element 9 in the form of, for example, an inner screw or set screw for fixing the rod 6 in the receiving part 5.

The receiving part 5 will be described in greater detail referring additionally to FIGS. 3a to 4d. The receiving part 5 includes first end 5a and an opposite second end 5b and a central axis C that passes through the first end 5a and the second end 5b. The first end 5a may serve as an abutment for a portion of the instrument as described in greater detail below. A passage 51 extends through the receiving part 5 from the first end 5a to the second end 5b. The passage 51 may be formed as a cylindrical coaxial bore 51a in a region from the first end 5a to a distance from the first end 5a and may in this embodiment narrow into an accommodation space 51b with an inner diameter that decreases towards the second end 5b until a region with a minimum diameter is reached. The accommodation space 51b serves for accommodating head 3 of the bone anchoring element 1 and at least a portion of the pressure member 7, as can be seen also in FIGS. 14a, 14b. Adjacent the second end 5b, a tapered or more specifically conically shaped bottom opening portion 51c extends from the region having the minimum diameter.

A substantially U-shaped recess 52 extends from the first end 5a in a direction of the second end 9b wherein a width of the recess 52 is slightly larger than a diameter of the rod 6, such that the rod 6 can be placed in the recess 52 and can be guided therein. The recess 52 forms a channel for the rod 6. By means of the recess 52, two free legs 52a, 52b are formed, on which an internal thread 53 may be provided. In this embodiment, the internal thread 53 extends from an annular end surface 10 defined by first end 5a up to a distance from the first end 5a inside the bore 51. The internal thread 53 can be, for example, a metric thread, a flat thread, a negative angle-thread, a saw-tooth thread or any other thread form. Meanwhile, the fixation element 9 in the form of an inner screw has a thread corresponding to the internal thread 53 provided on the legs 52a, 52b. Preferably, a thread form such as a flat thread or a negative angle thread is used to prevent or reduce the splaying of the legs 52a, 52b when the fixation element 9 is screwed-in. An undercut 59 is formed adjacent to internal thread 53 in a direction away from the first end 5a, as can be seen in FIG. 4a.

An upper part 50 of the receiving part 5 which is adjacent to the first end 5a has a substantially cylindrical outer surface except for example two flat recessed portions 56a, 56b, etc., which will be explained in more detail below. Also, at the outer surface of the upper part 50 of the receiving part 5, a first engagement structure for engagement with the instrument is provided, wherein the first engagement structure may be formed by two circumferential ribs 54a, 54b which are formed on each leg 52a, 52b in the embodiment shown, respectively. The ribs 54a, 54b are positioned between the top end 5a and a lower end 50a of the upper portion 50. Each of the ribs 54a, 54b extends over a segment of the circumference of the upper portion 50, for example, for approximately a quarter circle or less, for example by an angle of about 60° (see FIG. 4c) as in the embodiment shown. The arrangement is such that one end 540a1, 540b1 of each rib 54a, 54b is positioned at the recess 52 and the other end 540a2, 540b2 of each rib extends approximately to the middle section of each leg 54a, 54b as seen in a circumferential direction. Hence, in a circumferential direction, there is a rib-free surface portion 55a, 55b on the outer surface of each leg 52a, 52b which extends in that direction between the respective other end 540a2, 540b2 of the rib 54a, 54b and a respective other edge of U-shaped recess 52.

Furthermore, the ribs 54a, 54b are arranged in an asymmetric manner with respect to a plane extending through the central axis C of the coaxial bore 51 and a longitudinal axis L of the recess 52. More specifically, the position of the ribs 54a, 54b is offset by 180° measured in relation to the central axis C and is rotated with respect to the central axis C such that the rib 54a of the leg 52a extends to the rod receiving recess 52 at one side of the receiving part 5 and the rib 54b extends to the rod receiving recess 52 at the other side of the receiving part 5. This permits the instrument to be placed first onto the rib-free portions 55a, 55b and then to be rotated to engage the ribs 54a, 54b as described in greater detail below.

Figures 3A, 3B, 4A, 4B:
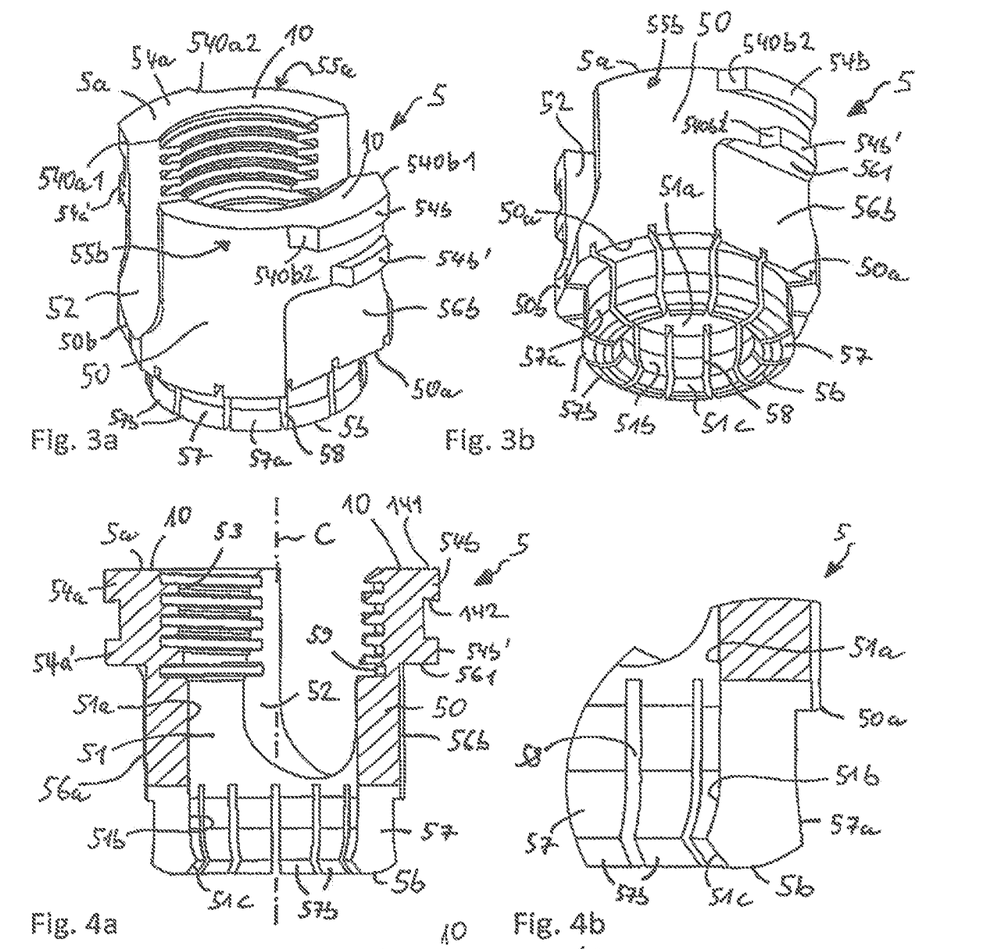
Figure 4C:
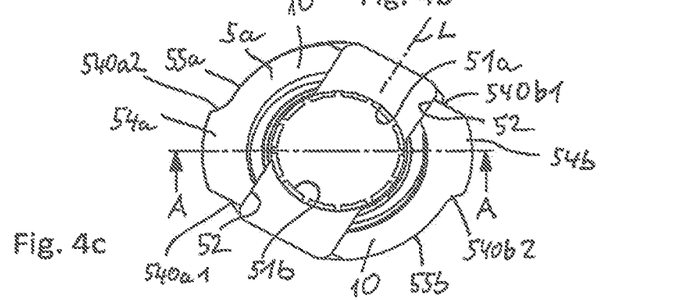
Figure 4D:
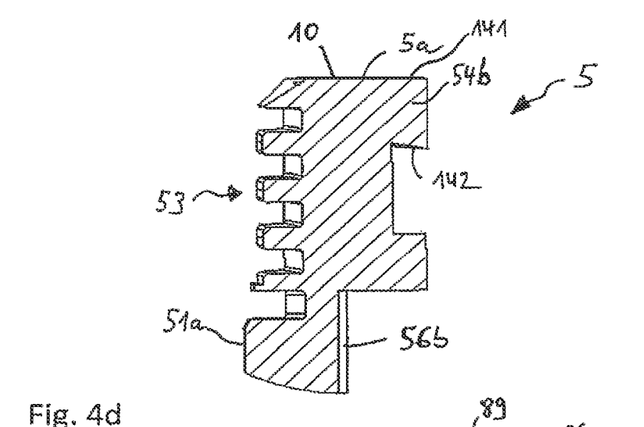
FIG. 4d shows a cross section of an upper part of the receiving part of FIG. 4a in an enlarged view.
Figure 17A:
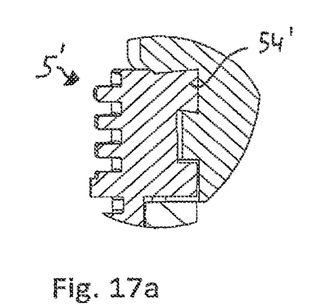
FIGS. 17a to 17c show alternative embodiments of engagement structures at a receiving part.

The ribs 54a, 54b may have a substantially rectangular cross-section or any other shape, but as can be seen in FIGS. 4a and 4d, a dovetail-shape which in this embodiment is single-sided is preferable. Namely, the ribs 54a, 54b include a horizontal upper surface 141 which extends substantially perpendicular to the central axis C, while a bottom surface 142 is inclined and extends radially downwards, i.e., towards the distal direction. In other words, a width of the ribs 54a, 54b increases in a direction radially outwards (as seen from the central axis C) allowing for a more stable and reliable connection with the instrument when a corresponding complementary profile is also provided therein. The horizontal upper surface 141 in this embodiment is flush with the annular end surface 10 of the legs 52a, 52b of the receiving part 5 which is provided at the first end 5a. Nevertheless, in an alternative embodiment illustrated in FIG. 17a, ribs 54' of modified receiving part 5' may also have a full two-sided dovetail-shape. The annular end surface 10 needs not to be planar. It may have an inclination directed inwards or outwards, or may be rounded. In preferred embodiments, the upper surface of the ribs 54a, 54b, 54' forming the first engagement structure is continuous with the annular end surface 10.

In any case, the ribs 54a, 54b and 54' in these embodiments are arranged directly at the annular end surface 10 of the legs 52a, 52b defined by the first end 5a of the receiving part 5, 5' or at least adjacent to that annular end surface 10 at first end 5a. Protrusions or recesses formed in the annular end surface are not ruled out, as long as the annular end surface 10 at first end 5a may serve as an abutment surface for the instrument as described below. A distance of the upper surface 141 of the ribs 54a, 54b from the annular end surface 10 of less than a width of the ribs in a direction parallel to the central axis C may be acceptable and is covered by the term "adjacent".

An advantage of the arrangement of ribs 54a, 54b at the top of the receiving part 5 directly at or adjacent to an annular end surface 10 at the first end 5a arises from the fact that the engagement features of the bone anchoring device are positioned away from the bone surface when the anchoring element is implanted within the bone and the head of the anchoring element is received in the accommodation space of the receiving part. This in turn allows that the instrument engages the device remote from the bone surface which avoids damages to the body tissue and permits to create small incisions. Also, this structure of the receiving part allows the engaging instrument to be configured more stable and sustainable, which will become clear from explanations with regard to the instrument below.

Figure 17B:
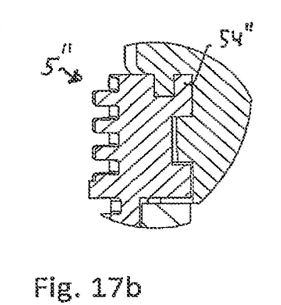
Figure 17C:
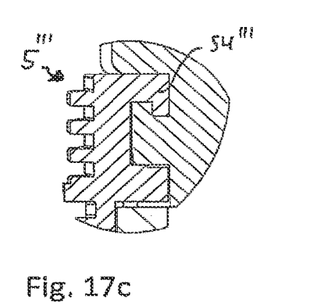

It is noted that the ribs may also have a substantially rectangular, trapezoidal, rhomboid-shaped, tooth-shaped or rounded cross-section, etc., or with regard to further modified receiving parts 5", 5''', the ribs 54", 54''' may even have complex shapes as illustrated in FIG. 17b or 17c, respectively. The ribs 54a, 54b may have inclined or rounded end portions. It shall be understood that a number of ribs is not limited to just one per leg 52a, 52b. More ribs may be implemented below the ribs 54a, 54b, such as stop ribs 54a', 54b' as examples of third engagement structures.

Stop ribs 54a', 54b' have a length less than that of the ribs 54a, 54b as can be seen in FIGS. 3a, 3b. Nevertheless, similar to ribs 54a, 54b, stop ribs 54a', 54b' extend from the rod receiving recess 52 at respective sides of the receiving part 5, and also extend in a distance and parallel to ribs 54a, 54b in a circumferential direction on the cylindrical outer surface of upper part 5. The cross section of stop ribs 54a', 54b' is in this embodiment rectangular as can be seen in FIG. 4a, but the same shapes as detailed with regard to ribs 54a, 54b are possible as well. Stop ribs 54a', 54b' may also include rounded and/or inclined end portions. The width may be equal to or less than that of ribs 54a, 54b, or may even be larger. In this embodiment, the width of stop ribs 54a', 54b' is smaller than that of ribs 54a, 54b. The stop ribs 54a', 54b' are arranged directly at or adjacent to an upper end wall 561 of recessed surface portions 56a, 56b.

As noted, the outer surface of the receiving part 5 also includes the substantially flat or planar recessed portions 56a, 56b. Recessed portions 56a, 56b are positioned at the upper part 50 in a circumferential direction in correspondence with the circumferentially extending ribs 54a, 54b and extend from an edge 50a at a bottom end of upper part 50 in a proximal direction parallel to the central axis C up to a predetermined distance from the ribs 54a, 54b. The recessed portions 56a, 56b need not have a planar flat surface recessed from a cylindrical outer contour of the receiving part 5 as in the embodiment but may also be rounded and/or provided with side walls. The recessed portions 56a, 56b serve as a guiding surface for upwardly projecting arms 83a, 83b of clamping ring 8 as will be detailed below.

Between the upper part 50 and the second end 5b of the receiving part 5 a head receiving portion 57 of the receiving part 5 is provided that includes the accommodation space 51b. The head receiving portion 57 also has a substantially cylindrical outer surface that has a smaller diameter than the diameter of the upper part 50 of the receiving part 5. Adjacent the second end 5b, there is a portion 57a of the outer surface that slightly tapers outwards. To allow insertion of the head 3, the head receiving portion 57 is flexible. In the embodiment shown, the head receiving portion 57 includes a plurality of flexible wall sections 57b that are separated by slits 58 extending in a longitudinal direction and being open towards the second end 5b. According to embodiments, the slits 58 may or may not extend even up into the upper part 50 of receiving part 5, as can be seen in FIGS. 3a and 3b. The number and size of the slits 58 is provided depending on the desired flexibility of the head receiving portion 57.

An inner diameter of the passage 51 at the second end 5b is smaller than a diameter of the head 3 of anchoring element 1. Due to the flexibility of the head receiving portion 57 the head 3 could be inserted from the second end 5b, but with the clamping ring 8 arranged in place embracing the head receiving portion 57, there is not sufficient expansion of the flexible wall sections 57b to allow insertion from the bottom end. In use, the anchoring element 1 in this embodiment will rather be inserted into the receiving part 5 via first end 5a (i.e., top loading).

The clamping ring 8 will be described in greater detail referring additionally to FIGS. 5a to 5d.

The clamping ring 8 comprises an upper end or first end 8a and an opposite lower end or second end 8b and may have a substantially spherical outer surface 81 which narrows towards the second end 8b. The outer diameter of the spherical surface 81 at or adjacent the first end 8a may be such that when the clamping ring 8 is mounted around the head receiving portion 57 of the receiving part 5, the outer spherical surface 81 of the clamping ring and the outer cylindrical surface of the upper part 50 of the receiving part 5 are flush with each other as depicted, for example, in FIG. 2. An inner diameter of the clamping ring 8 is such that the clamping ring 8 can be mounted around the head receiving portion 57 wherein the upper end 8a faces towards the bottom end or edge 50a of the upper part 50 of the receiving part 5. Alignment features in the form of flat portions 82 are provided at the outer surface 81 of the clamping ring 8. The flat portions 82 are offset by 180°. The alignment features may assist in aligning the clamping ring 8 correctly with respect to the receiving part 5, in particular with respect to further flat surfaces 50b recessed from the cylindrical outer surface of upper part 50 directly below the U-shaped recess 52, see FIG. 3a. It shall be noted, however, that the shape of the outer surface of clamping ring 8 may be different in other embodiments. For example, the outer surface 81 may have a cylindrical shape etc.

Figure 5A:
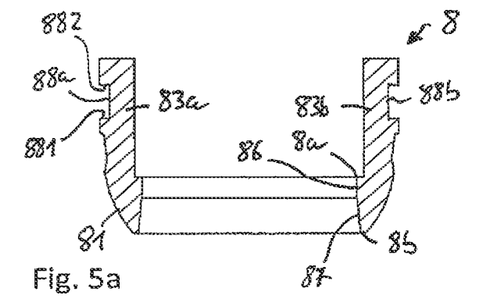
FIGS. 5a to 5d show a cross section, a top perspective view, a top view and a bottom perspective view of a clamping ring of FIG. 1.
Figure 5B:
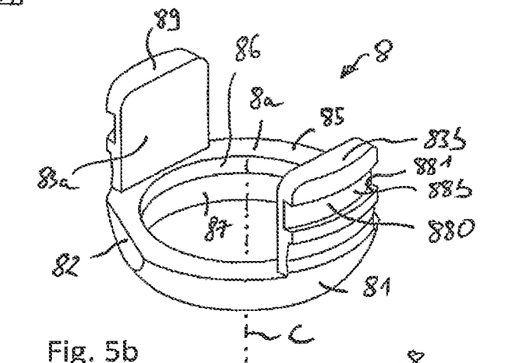

As can be seen in particular in FIG. 5a, clamping ring 8 further has a first inner cylindrical surface portion 86 that is adjacent or substantially adjacent to the upper end 8a. There may be a small inclined surface or beveled surface (not shown) provided adjacent to the upper end 8a to facilitate mounting. Adjacent or substantially adjacent to the lower end 8b, a second inner surface portion 87 of the clamping ring 8 may be tapered in such a manner that the inner diameter conically widens towards the lower end 8b. The second inner surface portion 87 is configured to cooperate with the outer surface portion 57a of the head receiving portion in such a manner that when the clamping ring 8 is moved towards a lowermost position on the head receiving portion 57, the cooperating surfaces 57a of the head receiving portion 57 and 87 of the clamping ring 8 exert an increasing inwardly directed radial force towards the head 3. Moreover, a height of the ring-shaped base portion (between ends 8a, 8b, i.e., without arms 83a, 83b) of clamping ring 8 in an axial direction, as can be seen in FIGS. 14a and 14b, corresponds substantially to a height of the head receiving portion 57 of the receiving part 5.

Figure 5C:
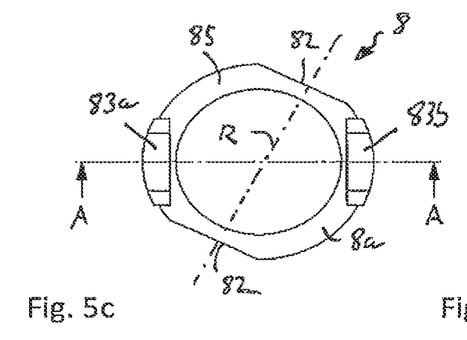
Figure 5D:
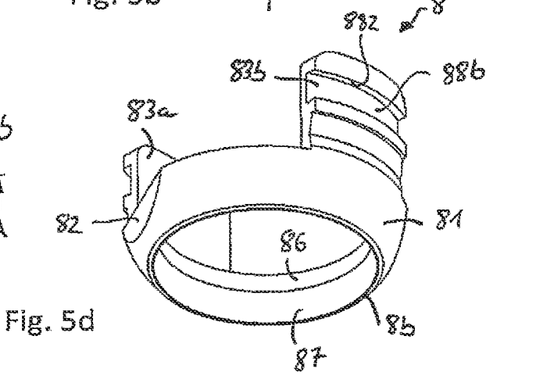

The clamping ring 8 includes two upwardly projecting arms 83a, 83b extending from a shoulder 85 formed at first end 8a. As can be seen particularly in FIGS. 2, 14a and 14b, the length of arms 83a, 83b substantially corresponds to a length of recessed portions 56a, 56b (as measured from the edge 50a at the bottom end of upper part 50) in a direction parallel to the central axis C, which are arranged to slideably receive arms 83a, 83b, when the clamping ring 8 is attached to the receiving part. Each of arms 83a, 83b has end faces 89 which may abut on—or at least may approach close to—upper end wall 561 of the recessed portions 56a, 56b. Similarly, the width of arms 83a, 83b substantially corresponds to that of recessed portions 56a, 56b. The two arms 83a, 83b are located diametrically opposite to each other and are positioned asymmetrically with respect to the flat portions 82. More specifically, the position of both arms 83a, 83b is rotated in the same direction by for example about 60° in this non-limiting embodiment with respect to flat portions 82 in the circumferential direction, which is indicated in FIG. 5c by the dash-dotted axis R that will be aligned with longitudinal axis L of the U-shaped recess 52 in an assembled state.

Each of the two upwardly projecting arms 83a, 83b includes an engagement structure for engagement with an instrument on its outer surface within or adjacent a tip portion of the respective arm which in this embodiment is provided as a dovetail-shaped circumferentially extending engagement structure formed as a notch 88a, 88b. As already noted above a consequence of such positioning at a tip portion of the arms 83a, 83b, the engagement structure of the clamping ring 8 as well as the engagement structure of the receiving part are located (i) close to each other and (ii) at a portion of a respective piece most proximate to the first end 5a of the receiving part 5 and away from the head receiving portion 57, i.e., away from the bone surface when the polyaxial bone anchoring device is in an assembled state in-situ. This allows to require less space within the body tissue by an instrument for performing steps of intermittent locking/unlocking during, e.g., repositioning of single vertebra or readjusting of a receiving part with an unlocked rod, wherein the clamping ring 8 is engaged and axially displaced by for example an outer tube of a locking/unlocking instrument with respect to an inner tube of the locking/unlocking instrument, which engages the receiving part 5. Examples of a similar instrument that can be used for locking and releasing a lock on a bone anchoring device, and similar interactions of such an instrument with other bone anchoring devices, are disclosed in U.S. Provisional Patent Application Ser. No. 62/371,029 and European Patent Application EP 16 182 818.1, the contents of which are hereby incorporated by reference in their entirety.

Figure 14A:
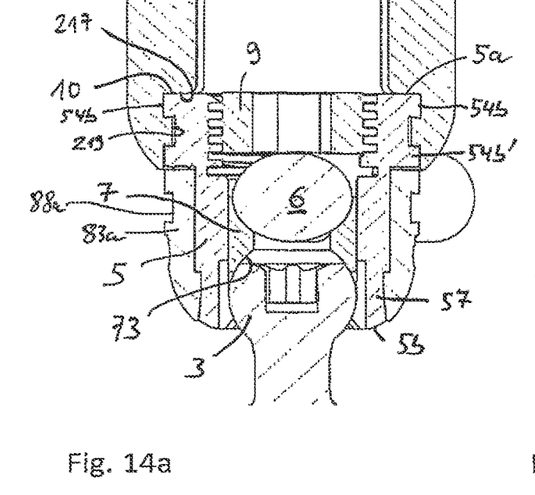
FIGS. 14a to 14b show cross sectional views of the instrument and polyaxial bone anchoring device in an engaged state.
Figure 14B:
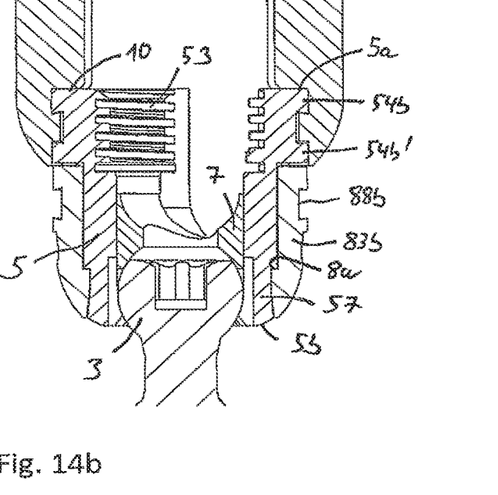

According to embodiments of the invention, the arms 83a, 83b have a sufficient length that the engagement structures provided on the arms, such as notches 88a, 88b, are arranged at an axial position in the direction of the central axis C corresponding to that of the rod 6 when the rod is received in the U-shaped recess 52 and pressed against the pressure member 7 (i.e., in a locked state of the bone anchoring device), preferably even at or above an axial position of a largest diameter of the rod 6 like in the embodiment illustrated herein, see FIGS. 14a, 14b.

In compliance with the dovetail-shaped cross sectional profile, a width of notches 88a, 88b decreases in a direction radially outwards towards the outer surface of arms 83b. The notches 88a, 88b include a cylindrical base surface 880 coaxial with the central axis C and correspondingly inclined bottom surfaces 881 and upper surfaces 882 as can be seen in more detail in FIG. 5a. It is noted that the engagement structure provided at the arms 83a, 83b need not be a notch 88a, 88b but may also be provided as a protruding rib as in the case of ribs 54a, 54b. Also, the cross sectional profile of the engagement structure formed as notches 88a, 88b or ribs may be substantially rectangular, trapezoidal, rhomboid-shaped, tooth-shaped or rounded, etc. instead of being dovetail-shaped.

A length of the engagement structures, e.g., notches 88a, 88b, is limited to the width of the arms 83a, 83b and substantially corresponds to that of the engagement structures of the receiving part, i.e., the circumferential ribs 54a, 54b. A depth of the recessed portions 56a, 56b and a thickness of the arms measured in radial direction is defined such that the cylindrical base surface 880 of notches 88a, 88b is substantially flush with the cylindrical outer surface of the receiving part 5, when the clamping ring is assembled with the receiving part. As a consequence, a dovetail-shaped circumferentially extending rib as an example of an engagement portion in an outer tube of the locking/unlocking instrument may be smoothly slid into a corresponding notch 88a, 88b of the clamping ring 8. However, a small step between the cylindrical outer surface of the receiving part 5 and base surface 880 of the notches 88a, 88b is not ruled out. Furthermore, it is not ruled out that further notches or ribs are provided at arms 83a, 83b.

The pressure member 7 as shown in FIGS. 1 and 14a, 14b comprises a substantially cylindrical outer surface 71 which has a diameter that is equal to or slightly smaller than an inner diameter of the cylindrical coaxial bore 51a to facilitate sliding and accommodation therein. Pressure member 7 also has a rod receiving portion 72 which is cylinder-segment shaped for receiving a rod 6 therein and which forms two legs opposite each other, which face the first end of the receiving part when the pressure member 7 is inserted in the coaxial bore 51a. Moreover, a spherical hollow section 73 is formed at a lower end of pressure member 7 which contacts the head 3 of anchoring element 1 and may exert pressure transferred from an inserted rod 6 onto the head 3 to lock the same when for example fixation element 9 is tightened. The pressure member may further comprise a coaxial hole allowing access to recess 4 which is provided in the head 3 of anchoring element 1.

The receiving part 5, the clamping ring 8, the pressure member 7, the fixation element 9 and the bone anchoring element 1 may be made of bio-compatible materials, for example of titanium or stainless steel, of a bio-compatible alloy, such as a NiTi-alloys, for example Nitinol, magnesium or magnesium alloys or from a bio-compatible plastic material, such as, for example, polyether ether ketone (PEEK) or poly-l-lactide acid (PLLA). The parts can be made of the same or of different materials.

In operation, the polyaxial bone anchoring device 100 is first assembled by attaching the clamping ring 8 to the flexible head receiving portion 57 via the second end 5b, wherein the flexible wall sections 57b are slightly compressed by the first and second inner surface portions 86, 87 of the clamping ring 8. Also, the bone anchoring element 1 is inserted into the receiving part 5 via the first end 5a. The pressure member 7 may then also be slid into the coaxial bore 51a of receiving part 5, and the anchoring element 1 is applied to a bone using, e.g., a driver or tool. A rod 6 may then be guided into the U-shaped recess 52 of receiving part 5 and using a locking/unlocking instrument the clamping ring is axially moved in the distal direction away from the first end 5a towards a lowermost position on the head receiving portion 57 to clamp the head 3, wherein the conical second inner surface portion 87 of clamping ring 8 cooperates with the outer surface portion 57a of the head receiving portion in such a manner that an increasing inwardly directed radial force is exerted towards and onto the head 3.

Thereby, the fixation element 9 needs not to be tightened yet. Rather, a locking/unlocking instrument allows a temporary clamping and/or unclamping via the actuating, i.e., moving clamping ring between a clamping position and a pre-locking position. This function permits the operator to readjust and fix an angular position of the receiving part with respect to the anchoring element even without an inserted rod, or to reposition individual vertebrae via the attached instrument. Nevertheless, final fixation will be effected by tightening the fixation element 9 and thus pressing the pressure member 7 against the head 3 to lock the same.

Figures 6, 7:
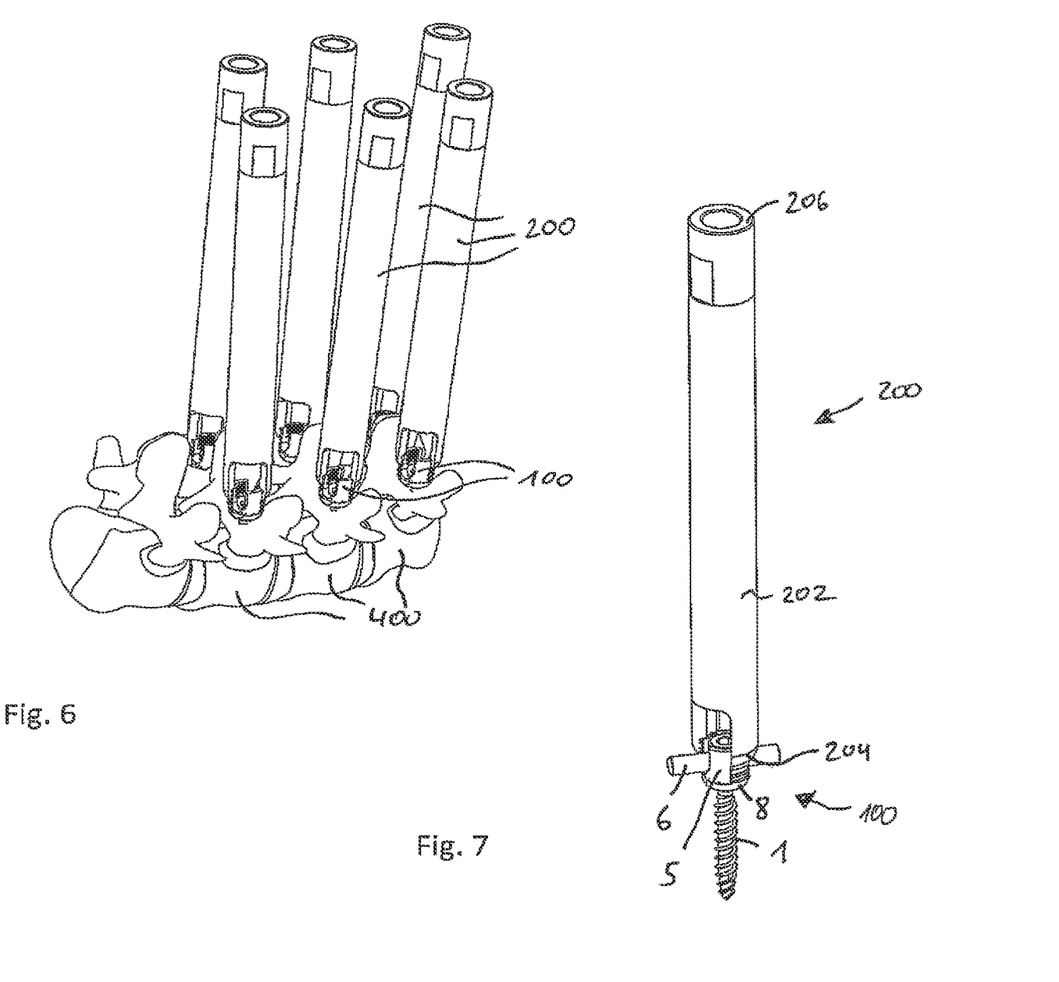
FIG. 6 shows a perspective view of multiple instruments according to an embodiment of the invention each engaging a polyaxial bone anchoring device according to FIG. 1.
FIG. 7 shows a perspective view of the instrument according to the embodiment and the polyaxial bone anchoring device in an engaged state.
Figures 8A, 8B, 9A, 9B:
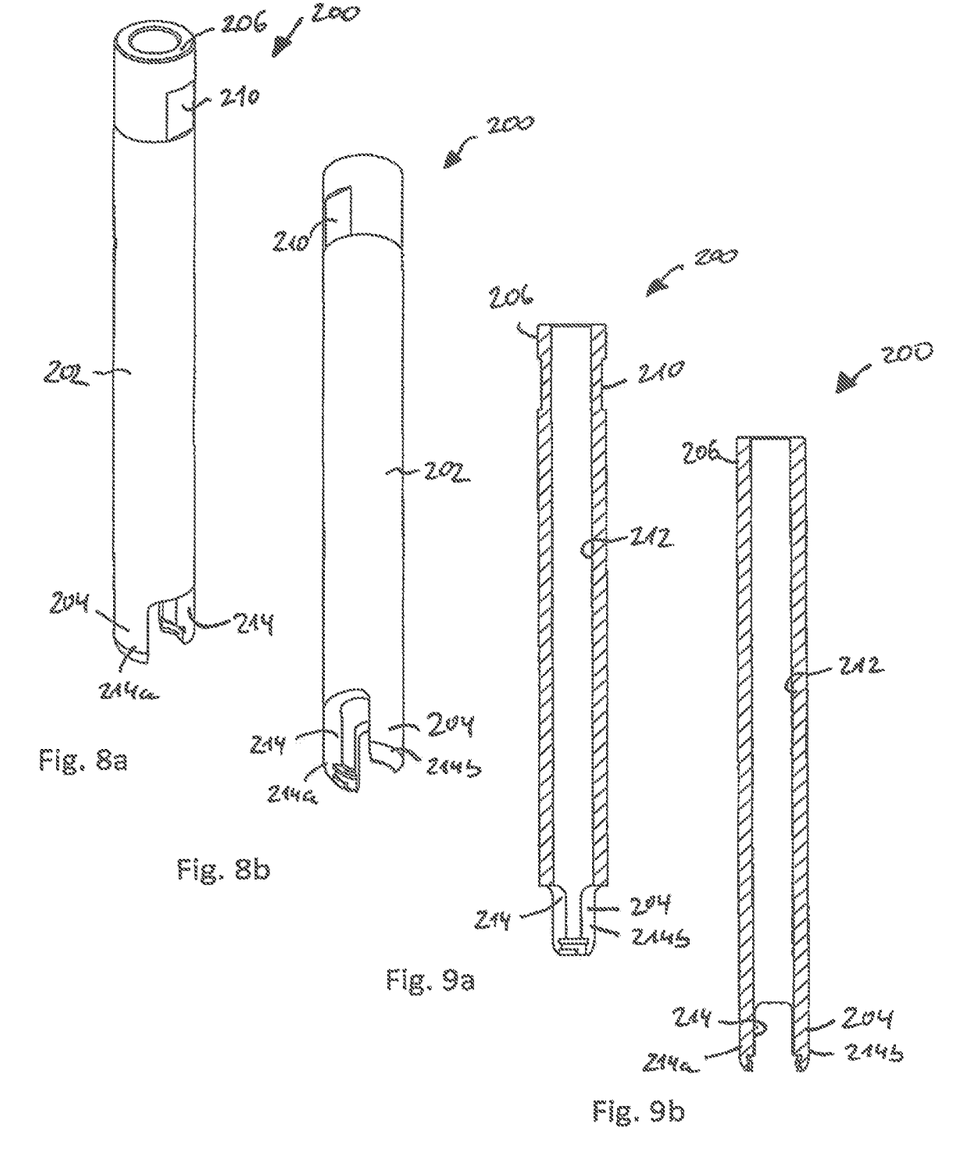
FIGS. 8a to 8b show perspective views from the top and the bottom of the instrument of FIG. 7.
FIGS. 9a to 9b show cross sectional views of the instrument of FIG. 7 in two different views perpendicular to each other.

Next, an instrument 200 for use with the polyaxial bone anchoring device 100 will be explained with reference to FIGS. 6-12. The instrument 200 functions as a head extension device which is configured to be attached to the receiving part 5 in-situ and thereby allows manipulating the receiving part 5 or supplying further instruments and/or parts to the receiving part 5. Multiple such instruments 200 may be attached to respective polyaxial bone anchoring devices 100 in-situ as illustrated in FIG. 6, the polyaxial bone anchoring devices 100 being positioned within vertebrae, respectively. Unlike the above explained instrument for locking/unlocking the clamping ring 8, which also engages the clamping ring 8 in addition to the receiving part 5, the instrument 200 is arranged to only engage the ribs 54a, 54b at the receiving part. Nevertheless, embodiments of any instruments such as the above described locking/unlocking instrument that are also configured to engage receiving part 5 of polyaxial bone anchoring device 100 disclosed herein are encompassed by the appended claims.

The instrument 200 includes a tubular member 202 having a front end portion 204, which comprises engagement portions for engagement with the engagement structures of the receiving part, and a rear end portion 206 as can be seen in FIG. 7.

As shown in FIGS. 8a-9b, the tubular member 202 includes an inner bore 212 extending from the rear end portion 206 to the front end portion 204, and the front end portion 204 is provided with a substantially rectangular-shaped recess 214 into which the bore 212 opens, and which forms two free legs 214a, 214b. The inner bore 212 has a diameter smaller than that of the receiving part 5. Inner bore 212 ends at an annular abutment surface 217, which serves to abut on annular end surface 10 of receiving part 5 during engagement. The tubular member 202 further has recessed portions 210 at opposite sides thereof in a region of the rear end portion 206, which may serve for attaching further instruments or for gripping the instrument.

Figure 10:
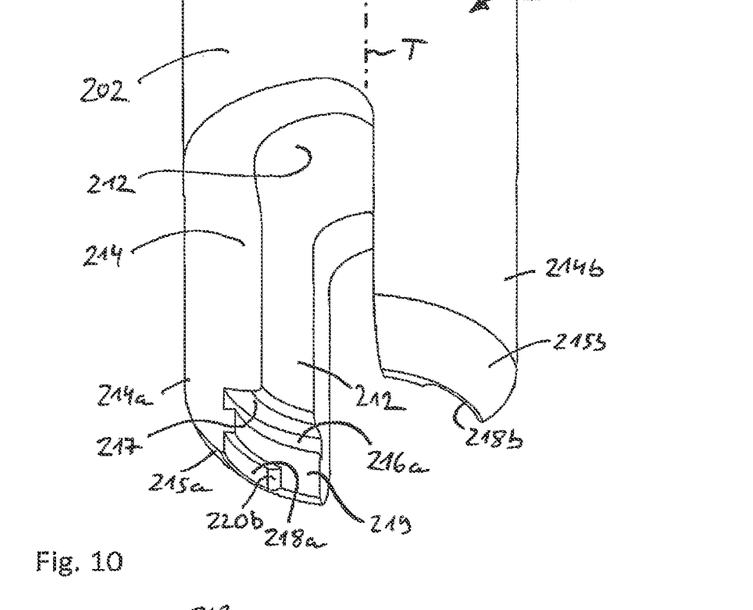
FIG. 10 shows an enlarged perspective view of a front end portion of the instrument of FIG. 7.
Figure 11:
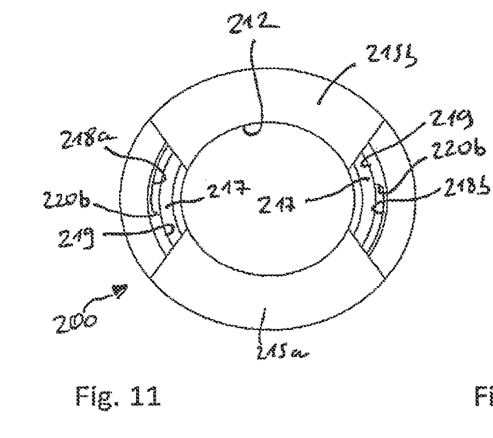
FIG. 11 shows a view onto the front end portion of FIG. 10 along a central axis of the instrument of FIG. 7.

As can be seen in FIG. 10, the legs 214a, 214b each includes a rounded tip portion 215a, 215b, respectively, which facilitates insertion of the instrument into the incision or hole in the tissue and guiding to the in-situ position of the receiving part 5. A length of the rounded tip portion 215a, 215b in a direction of a central axis T of the instrument is small compared to the portion of the free legs which has a substantially cylindrical contour and constant width measured in a radial direction from the central bore 212.

At an inner surface of the instrument in a region of the tip portion 215a, 215b of the free legs of the frond end portion 214 there are provided two engagement portions in the form of notches 216a, 216b. These notches 216a, 216b have a single-sided dove-tail-shaped cross section, which is complementary to that of the ribs 54a, 54b provided at the receiving part 5. Notches 216a, 216b are configured to slideably receive the ribs 54a, 54b during engagement by rotation in a circumferential direction as will be detailed below. Notches 216a, 216b extend between the recess walls and open into the recess 214 on both sides thereof in the circumferential direction around central axis T and have a length which corresponds to that of ribs 54a, 54b, covering for example an angle of 45°. As with regard to ribs 54a, 54b, the cross section may be different from a (single sided) dovetail-shape. Also the length may vary and depends on the width of the legs 214a, 214b.

Moreover, second engagement portions in the form of stop notches 218a, 218b are provided directly at the edge of the tip portions 215a, 215b extending from the recess at one open end 220a thereof in a circumferential direction around central axis T. More specifically, the notches 218a, 218b have a length shorter than that of notches 216a, 216b. As a consequence, stop notches 218a, 218b include an end or abutment face 220b facing in a circumferential direction, in this embodiment facing in the counter-clockwise direction in both cases.

Stop notches 218a, 218b are configured to slideably receive stop ribs 54a', 54b' therein during engagement by rotation in a circumferential direction as will be detailed below. However, as a consequence of the abutment faces 220b, rotational movement of the instrument 200 with respect to the receiving part 5 is limited by these abutment faces 220b functioning as a stop. Advantageously, such stop guarantees that the instrument 200 attains a correctly aligned engagement position with respect to the receiving part 5 and does not unintentionally lose contact with the receiving part during use, which otherwise might be harmful for the patient and also might damage the engagement features.

Still further, as can be seen in FIG. 10, the stop notches 218a, 218b do no need to have a lower wall. Rather, the notches 218a, 218b are also open towards the distal direction, i.e., towards second end 5b of receiving part 5. Since an axial position of the instrument 200 with respect to the receiving part 5 is already defined by ribs 54a, 54b received in notches 216a, 216b, the lower walls can be omitted and the stop notches 218a, 218b herein merely provide for the stop function. Due to the omission of the lower walls, the tip edge of instrument 200 is further closer to the ribs 54a, 54b seen in the axial direction, which further reduces the depth with which the instrument has to enter the incision in order to engage the receiving part. This feature further avoids delicate parts arranged near the tip and the engagement portions which inevitably undergo large lever actions during use.

Figure 12:
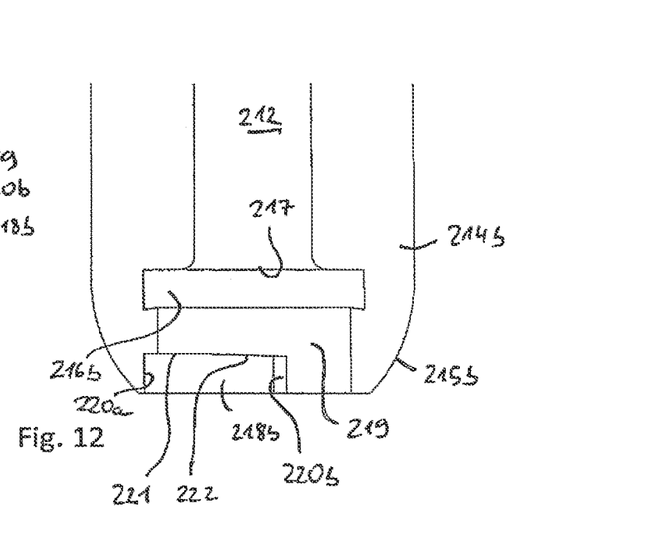
FIG. 12 shows a side view of the inner wall surface of one of the legs of the front end portion of the instrument.

As can be seen in FIG. 12, the stop notches nevertheless have an upper guiding wall, which, however, has two sections, namely an annular horizontal section 221 which extends in a plane perpendicular to the central axis T, and an inclined section 222. The horizontal section 221 is located extending from the open end 220a of notches 218a, 218b, while the inclined section 222 extends adjacent to horizontal section 221 up to the abutment face 220b at the other end of notches 218a, 218b. The inclination is such that the width of notches 218a, 218b narrows towards the abutment end 220b. As a consequence, during sliding-in of a rib 54a', 54b' received in one of the notches 218a, 218b from the open end 220a in a rotational movement towards the abutment face 220b, such rib 54a', 54b' eventually contacts the inclined surface which in turn creates a frictional force between the rib 54a', 54b' and the inclined surface 222.

Advantageously, this function on the one hand assists in maintaining an engaged state of the instrument 200 with the receiving part 5 and prevents unintentional loosening. On the other end, the operator obtains a tactile response during the rotational movement of the instrument that he is approaching the stop.

It is noted that between the notches 54a and 54a' as well as between notches 54b and 54b' there extends a cylindrical inner surface 219, which as compared with the inner surface of inner bore 212 has an enlarged diameter, which corresponds to the diameter of the outer cylindrical surface of the upper part 50 of the receiving part 5. This cylindrical inner surface 219 serves for guiding the instrument while placing the instrument on the receiving part 5 as will be explained in the following.

Figure 13A:
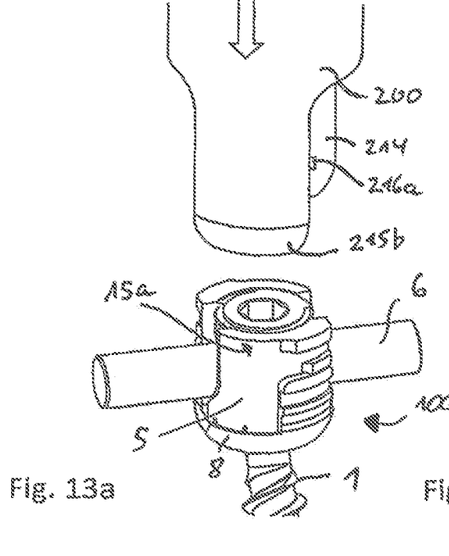
FIGS. 13a to 13d show steps of engaging the polyaxial bone anchoring device using the instrument of FIG. 7.

A use of the instrument 200 and the polyaxial bone anchoring device 100 is shown in FIGS. 13a-d. As shown in FIG. 13a the instrument 200 is moved to the receiving part 5 in a direction of the central axes C, T being aligned with each other. Thereby, the free legs 214a, 214b are aligned with the rib-free portions 55a, 55b of the receiving part 5, respectively, in a circumferential direction.

Figure 13B:
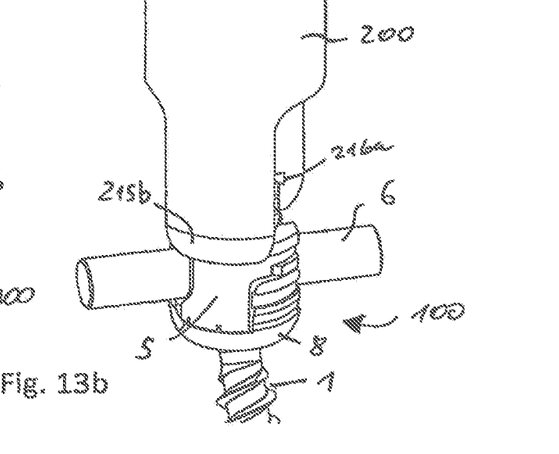

In FIG. 13b, the instrument 200 is guided over the receiving part 5. The cylindrical inner surface 219 of the instrument 200 slideably contacts the outer cylindrical surface of the upper part of the receiving part 5 and crosses the rib-free portions 55a, 55b.

Figure 13C:
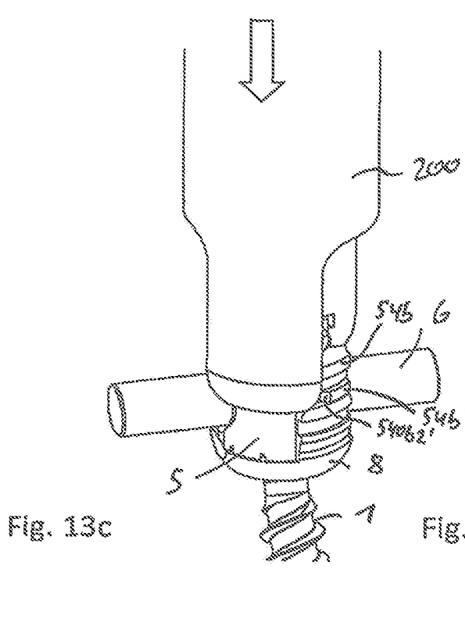

In FIG. 13c, the downward movement of the instrument 200 stops wherein the annular abutment surface 217 at the end of bore 212 abuts on the annular end surface 10 of the receiving part. The rounded tip portion 215a, 215b having the engagement portions arranged at its inner wall is in this situation located at an axial position of the engagement structures 54a, 54b, 54a', 54b'.

Figure 13D:
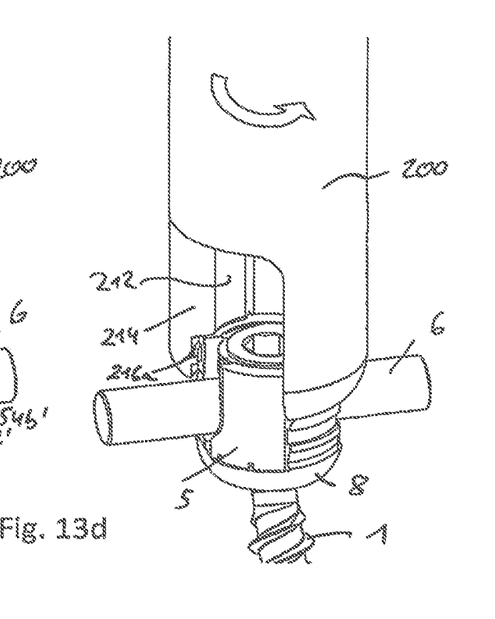

In FIG. 13d, the instrument 200 is rotated in the circumferential direction as indicated by the arrow. Thereby, the ribs 54a, 54b of the receiving part 5 slide with leading end portions 540a2, 540b2 into the respective notches 216a, 216b of the instrument 200, and the ribs 54a', 54b' slide with leading end portions 540a2', 540b2' into the respective notches 218a, 218b of the instrument 200. Initially, the inclined surface 222 has contacted an upper surface of ribs 54a', 54b' creating an increasing friction and slight tension between the ribs 54a and 54a' as well as 54b and 54b'. Finally, leading end portions 540a2', 540b2' of each of ribs 54a', 54b' abuts on respective abutment faces 220b. The increasing friction thereby leads to self-locking of the engagement between the receiving part 5 and the instrument, whereby the abutment serves to define an aligned endpoint of the rotational movement.

Figure 15:
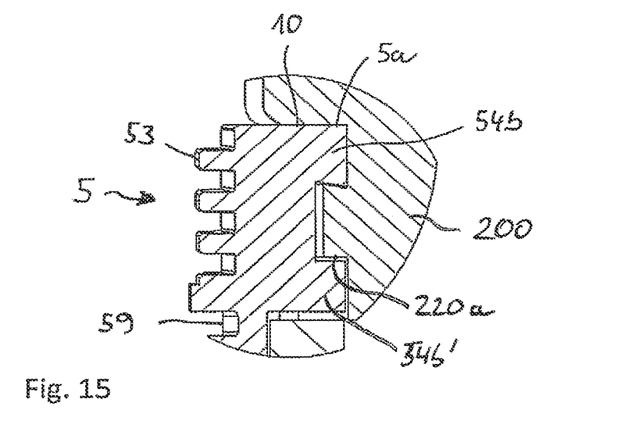
FIG. 15 shows an enlarged view of engagement portions and structures of the instrument and the polyaxial bone anchoring device in an engaged state, respectively.
Figure 16A:
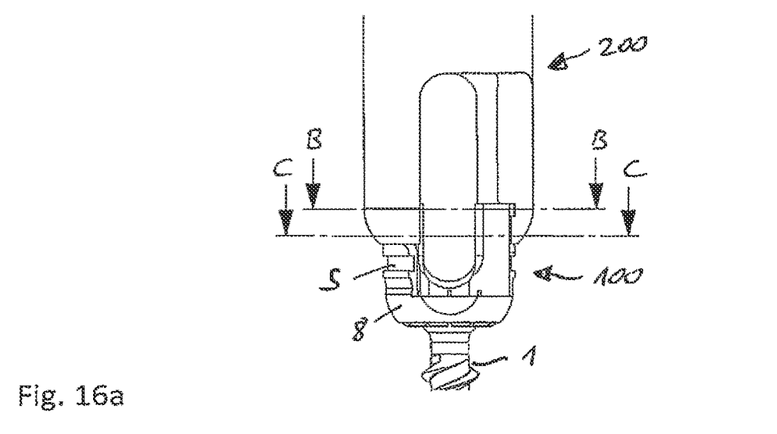
FIG. 16a shows a side view of the instrument and the polyaxial bone anchoring device in an engaged state.
Figures 16B, 16C:
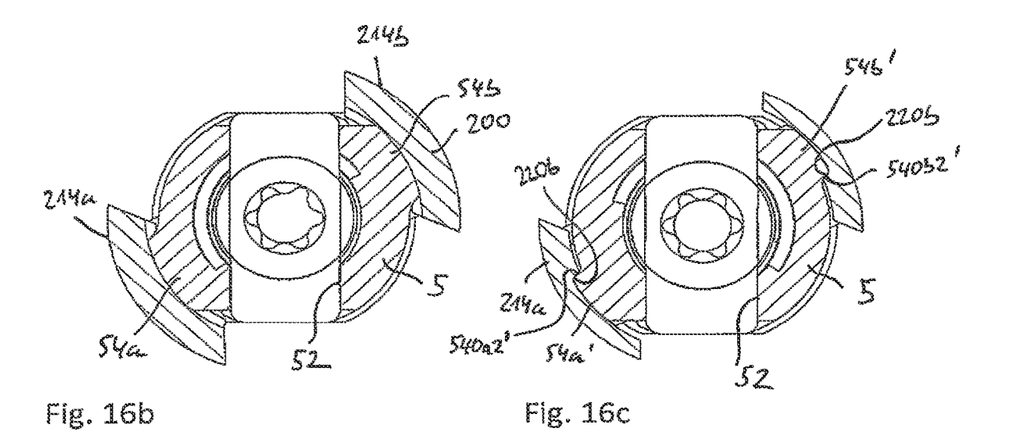

In this final engagement position, which is also shown in FIGS. 14a and 14b, the operator may perform desired steps of assembling and orienting the polyaxial bone anchoring device. FIG. 15 shows an enlarged detail of the engagement structures and portions. FIGS. 16b and 16c reveal horizontal cross sections in the engaged position.

Various modifications may be made without departing from the scope defined by the appended claims. For example, as noted above, the instrument may be different from the head extension instrument and may for example be a locking/unlocking instrument.

Moreover, the polyaxial bone anchoring device may include a pressure member formed as an inner cap itself having a flexible head receiving portion as described for example in European Patent Application EP 16 182 818.1, wherein a head of an anchoring element may be loaded to a head receiving portion of a receiving part from the bottom. In that case, the ribs disclosed therein for example in FIG. 3 are replaced with an arrangement of ribs as explained above while all other features are maintained.

However, it may also be conceived to add arms 83a, 83b as described above to the clamping ring disclosed in European Patent Application EP 16 182 818.1 to bring the ribs of the clamping ring and the receiving part into closer proximity like in the embodiment presented above.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device comprising:
    a bone anchoring element comprising a head and a shank;
    a receiving part for coupling a rod to the bone anchoring element, the receiving part comprising a first end, a second end below the first end, a central axis extending between the first end and the second end, a recess at the first end for receiving the rod, and a head receiving portion at the second end for pivotably holding the head of the bone anchoring element;
    a pressure member positionable in the receiving part and configured to exert pressure on the head when the head is held in the head receiving portion, wherein the pressure member is configured to directly engage a portion of the head above a greatest diameter of the head measured in a direction perpendicular to the central axis while remaining spaced apart from every portion of the head below the greatest diameter; and a closed ring configured to be assembled directly to the head receiving portion from the second end of the receiving part;

wherein when the head of the bone anchoring element and the pressure member are in the receiving part and the closed ring is assembled to the head receiving portion with an abutment on the head receiving portion securing the closed ring from separating from the head receiving portion, the bone anchoring device is configured to assume a first configuration where the head is pivotable relative to the receiving part, and where at least part of each of the head receiving portion and the closed ring extends to an axial position that is lower than an axial position of the greatest diameter of the head; and wherein the bone anchoring device is adjustable from the first configuration to a second configuration where an axial position of the closed ring relative to a compressible portion of the bone anchoring device is adjusted such that the closed ring exerts a radial force on the compressible portion to clamp the head and restrict pivoting of the head relative to the receiving part.

2. The bone anchoring device of claim 1, wherein the closed ring is positionable around the head receiving portion.

3. The bone anchoring device of claim 1, wherein the closed ring comprises an upwardly projecting arm.

4. The bone anchoring device of claim 1, wherein the compressible portion is formed on the head receiving portion of the receiving part.

5. The bone anchoring device of claim 1, wherein when the head is in the head receiving portion, the head receiving portion is configured to directly contact the head.

6. The bone anchoring device of claim 1, wherein the entire pressure member remains axially above the greatest diameter of the head in both the first and second configurations.

7. The bone anchoring device of claim 1, wherein an axial position of the closed ring relative to the entire receiving part changes when the bone anchoring device is adjusted from the first configuration to the second configuration.

8. The bone anchoring device of claim 1, wherein the closed ring is configured to exert the radial force directly on the head receiving portion in the second configuration.

9. The bone anchoring device of claim 1, wherein the closed ring comprises an engagement structure configured to engage an instrument when the instrument is connected to the bone anchoring device from the first end of the receiving part.

10. A bone anchoring device comprising:

a receiving part for coupling a rod to a bone anchoring element, the receiving part comprising a first end, a second end below the first end, a central axis extending between the first end and the second end, a recess extending from the first end towards the second end for receiving the rod, the recess forming two legs, and a head receiving portion at the second end for pivotably holding a head of the bone anchoring element; and a clamping element movable relative to the receiving part from a first position wherein an inserted head is pivotable relative to the receiving part, to a second position wherein the clamping element locks the head relative to the receiving part;

wherein the receiving part further comprises an abutment that is formed monolithically with one of the two legs and that is configured to directly engage the clamping element such that the entire clamping element remains axially below the abutment in both the first and second positions; and wherein the clamping element comprises an engagement structure positionable adjacent axially to the abutment to engage an instrument when the instrument is connected to the bone anchoring device from the first end of the receiving part, and wherein at least part of the engagement structure is movable to an axial position that is higher than an axial position of a largest diameter of a rod that is received in the recess.

11. The bone anchoring device of claim 10, wherein the clamping element is positionable around the head receiving portion.

12. The bone anchoring device of claim 11, wherein the clamping element is configured to exert a radial force directly on the head receiving portion in the second position to lock the head relative to the receiving part.

13. The bone anchoring device of claim 10, wherein an axial position of the clamping element relative to the receiving part in the first position is different from an axial position of the clamping element relative to the receiving part in the second position.

14. The bone anchoring device of claim 13, wherein the axial position of the clamping element relative to the receiving part is lower in the second position compared to the first position.

15. The bone anchoring device of claim 10, wherein when the head is in the head receiving portion, the head receiving portion is configured to directly contact the head.

16. The bone anchoring device of claim 10, wherein the engagement structure of the clamping element is formed at a top end of the clamping element.

17. The bone anchoring device of claim 10, wherein the engagement structure is configured to be arranged asymmetric with respect to a plane extending through the central axis of the receiving part and through a longitudinal axis of the recess for the rod.

18. The bone anchoring device of claim 10, wherein the receiving part comprises a corresponding engagement structure configured to engage the instrument when the instrument engages the engagement structure of the clamping element.

19. The bone anchoring device of claim 18, wherein the engagement structure of the clamping element and the corresponding engagement structure of the receiving part are configured to be axially aligned with one another around a circumference of the bone anchoring device.

20. A bone anchoring device comprising:

a receiving part for coupling a rod to a bone anchoring element, the receiving part comprising a first end, a second end below the first end, a central axis extending between the first end and the second end, a recess at the first end for receiving the rod, and a head receiving portion at the second end for pivotably holding a head of the bone anchoring element;

a pressure member positionable in the receiving part and configured to exert pressure on the head when the head is held in the head receiving portion of the receiving part; and a clamping element movable relative to the receiving part from a first position wherein an inserted head is pivotable relative to the receiving part, to a second position wherein the clamping element locks the head relative to the receiving part;
wherein the receiving part further comprises an abutment that is configured to directly engage the clamping element such that the entire clamping element remains axially below the abutment in both the first and second positions; and
wherein the clamping element comprises an engagement structure positionable adjacent axially to the abutment to engage an instrument when the instrument is connected to the bone anchoring device from the first end of the receiving part, and wherein at least part of the engagement structure is movable to an axial position that is higher than an axial position of a largest diameter of a rod that is received in the recess.

\* \* \* \* \*